US008870878B2

(12) United States Patent
Gorek (10) Patent No.: US 8,870,878 B2
(45) Date of Patent: Oct. 28, 2014

(54) MINIMALLY INVASIVE RETRACTOR AND METHODS OF USE

(75) Inventor: Josef Gorek, Ross, CA (US)

(73) Assignee: K2M, Inc., Leesburg, VA (US)

(*) Notice: Subject to any disclaimer, the term of this patent is extended or adjusted under 35 U.S.C. 154(b) by 74 days.

(21) Appl. No.: 13/105,965

(22) Filed: May 12, 2011

(65) Prior Publication Data

US 2011/0209821 A1 Sep. 1, 2011

Related U.S. Application Data

(62) Division of application No. 12/396,052, filed on Mar. 2, 2009.

(60) Provisional application No. 61/032,140, filed on Feb. 28, 2008.

(51) Int. Cl.
  A61B 17/70   (2006.01)
  B29C 45/14   (2006.01)
  A61B 17/02   (2006.01)
  B29L 31/00   (2006.01)
  A61B 19/00   (2006.01)

(52) U.S. Cl.
  CPC ....... B29C 45/14311 (2013.01); A61B 17/7085 (2013.01); A61B 17/0218 (2013.01); B29L 2031/7546 (2013.01); A61B 17/7037 (2013.01); A61B 17/0206 (2013.01); A61B 2019/307 (2013.01); B29C 2045/14327 (2013.01)
  USPC .......................... 606/86 A; 606/104; 606/266

(58) Field of Classification Search
  USPC .......................... 606/246–279, 104
  See application file for complete search history.

(56) References Cited

U.S. PATENT DOCUMENTS

| | | | |
|---|---|---|---|
| 3,129,706 A | 4/1964 | Reynolds | |
| 3,486,505 A | 12/1969 | Morrison | |
| 4,950,269 A * | 8/1990 | Gaines, Jr. | 606/261 |
| 5,242,443 A | 9/1993 | Kambin | |
| 5,431,658 A | 7/1995 | Moskovich | |
| 5,496,321 A | 3/1996 | Puno | |
| 5,545,165 A | 8/1996 | Biedermann | |
| 5,554,157 A * | 9/1996 | Errico et al. | 606/264 |
| 5,582,577 A | 12/1996 | Lund | |
| 5,685,826 A | 11/1997 | Bonutti | |
| 5,797,911 A | 8/1998 | Sherman | |
| 5,902,231 A | 5/1999 | Foley et al. | |
| 5,944,658 A | 8/1999 | Koros et al. | |
| 6,063,088 A | 5/2000 | Winslow | |

(Continued)

FOREIGN PATENT DOCUMENTS

WO WO 2007/084641 7/2007

*Primary Examiner* — Jerry Cumberledge
(74) *Attorney, Agent, or Firm* — Carter DeLuca Farrell & Schmidt LLP (57) ABSTRACT

A device, system and method for orthopedic spine surgery using a novel screw-based retractor, disclosed herein, that allows for access to the spine through a minimally or less invasive approach. The retractor device is designed as a co-molded part of the tulip of a pedicle screw assembly with opposed arms of the retractor spread apart to open the wound proximally. The arms are removed by separating the arms from the tulip and removing them from the incision. The retractor device is intended to be made of a relatively stiff material, sterile packaged and disposable after one use. A system and method for using the retractor and performing a minimally invasive spine surgical procedure are also disclosed.

20 Claims, 5 Drawing Sheets

(56) References Cited

U.S. PATENT DOCUMENTS

| | | | |
|---|---|---|---|
| 6,083,225 A | 7/2000 | Winslow et al. | |
| 6,099,547 A | 8/2000 | Gellman et al. | |
| 6,102,951 A | 8/2000 | Sutter | |
| 6,146,385 A | 11/2000 | Torrie et al. | |
| 6,187,000 B1 | 2/2001 | Davison et al. | |
| 6,200,322 B1 | 3/2001 | Branch et al. | |
| 6,206,826 B1 | 3/2001 | Mathews et al. | |
| 6,270,501 B1 | 8/2001 | Freiberg et al. | |
| 6,280,442 B1 | 8/2001 | Barker | |
| 6,358,253 B1 | 3/2002 | Torrie et al. | |
| 6,360,750 B1 | 3/2002 | Gerber et al. | |
| 6,478,800 B1 | 11/2002 | Fraser et al. | |
| 6,485,494 B1 | 11/2002 | Haider | |
| 6,530,926 B1 | 3/2003 | Davison | |
| 6,530,929 B1 | 3/2003 | Justis et al. | |
| 6,616,605 B2 | 9/2003 | Wright | |
| 6,652,533 B2 | 11/2003 | O'Neil | |
| 6,669,729 B2 | 12/2003 | Chin | |
| 6,740,091 B2 | 5/2004 | Kohrs et al. | |
| 6,743,206 B1 | 6/2004 | Smith | |
| 6,755,841 B2 | 6/2004 | Fraser et al. | |
| 6,796,422 B1 | 9/2004 | Lu | |
| 6,800,084 B2 | 10/2004 | Davison et al. | |
| 6,849,064 B2 | 2/2005 | Hamada | |
| 6,929,606 B2 | 8/2005 | Ritland | |
| 7,008,422 B2 | 3/2006 | Foley et al. | |
| 7,011,660 B2 | 3/2006 | Sherman et al. | |
| 7,056,321 B2 | 6/2006 | Pagliuca et al. | |
| 7,083,621 B2 | 8/2006 | Shaolian et al. | |
| 7,108,705 B2 | 9/2006 | Davison et al. | |
| 7,144,393 B2 | 12/2006 | DiPoto et al. | |
| 7,160,300 B2 | 1/2007 | Jackson | |
| 7,166,107 B2 | 1/2007 | Anderson | |
| 7,179,261 B2 | 2/2007 | Sicvol et al. | |
| 7,188,626 B2 | 3/2007 | Foley et al. | |
| 7,250,052 B2 | 7/2007 | Landry | |
| 7,491,208 B2 | 2/2009 | Pond, Jr. et al. | |
| 7,563,264 B2 * | 7/2009 | Landry et al. | 606/86 A |
| 7,717,942 B2 * | 5/2010 | Schumacher | 606/266 |
| 8,251,901 B2 * | 8/2012 | White et al. | 600/210 |
| 2003/0004401 A1 | 1/2003 | Ball | |
| 2003/0191371 A1 | 10/2003 | Smith | |
| 2004/0138662 A1 | 7/2004 | Landry et al. | |
| 2004/0143265 A1 | 7/2004 | Landry et al. | |
| 2005/0065517 A1 | 3/2005 | Chin | |
| 2005/0131408 A1 * | 6/2005 | Sicvol et al. | 606/61 |
| 2005/0131421 A1 | 6/2005 | Sicvol et al. | |
| 2005/0154389 A1 | 7/2005 | Selover et al. | |
| 2005/0165408 A1 | 7/2005 | Puno et al. | |
| 2005/0182410 A1 * | 8/2005 | Jackson | 606/73 |
| 2005/0215999 A1 | 9/2005 | Birkmeyer et al. | |
| 2006/0025771 A1 | 2/2006 | Jackson | |
| 2006/0052782 A1 * | 3/2006 | Morgan et al. | 606/60 |
| 2006/0074445 A1 | 4/2006 | Gerber et al. | |
| 2006/0200135 A1 | 9/2006 | Sherman et al. | |
| 2006/0229614 A1 | 10/2006 | Foley et al. | |
| 2006/0247658 A1 | 11/2006 | Pond et al. | |
| 2006/0264962 A1 | 11/2006 | Chin et al. | |
| 2007/0049931 A1 | 3/2007 | Justis et al. | |
| 2007/0055247 A1 | 3/2007 | Jahng | |
| 2007/0106123 A1 | 5/2007 | Gorek | |
| 2007/0129731 A1 | 6/2007 | Sicvol et al. | |
| 2007/0167954 A1 | 7/2007 | Sicvol et al. | |
| 2008/0114403 A1 | 5/2008 | Kuester et al. | |
| 2008/0119849 A1 | 5/2008 | Beardsley et al. | |
| 2008/0161857 A1 * | 7/2008 | Hestad et al. | 606/264 |
| 2008/0275456 A1 * | 11/2008 | Vonwiller et al. | 606/99 |
| 2009/0131755 A1 | 5/2009 | White et al. | |
| 2009/0221877 A1 | 9/2009 | Woods | |
| 2009/0221879 A1 | 9/2009 | Gorek | |
| 2009/0222044 A1 | 9/2009 | Gorek | |
| 2009/0222046 A1 | 9/2009 | Gorek | |
| 2009/0259256 A1 * | 10/2009 | Miller | 606/250 |
| 2011/0054259 A1 | 3/2011 | Gorek | |

* cited by examiner

MINIMALLY INVASIVE RETRACTOR AND METHODS OF USE

CROSS-REFERENCE TO RELATED APPLICATIONS

This application is a divisional of co-pending U.S. patent application Ser. No. 12/396,052, filed Mar. 2, 2009, which claims the benefit of, and priority to, U.S. Provisional Patent Application No. 61/032,140, filed Feb. 28, 2008, the entire contents of both of which are incorporated herein by reference.

BACKGROUND

1. Technical Field

The present disclosure relates generally to orthopaedic spine surgery and in particular to a minimally invasive retractor and methods for use in a minimally invasive surgical procedure.

2. Background of the Technology

There has been considerable advancement in the development of retractors and retractor systems that are adapted for use in less invasive procedures. Many of the recent developments are based on traditional types of surgical retractors for open procedures, predominantly table-mounted devices of various designs. These devices tend to be cumbersome and are not well adapted for use in small incisions. Standard hand-held surgical retractors are well known in the prior art and can be modified to fit the contours of these small incisions, but they require manual manipulation to maintain a desired placement, thereby occupying one hand of the physician or requiring another person to assist the physician during the procedure. Typical retractors are also positioned into the soft tissue and are levered back to hold the wound open, frequently requiring re-positioning if they dislodge, obstruct the physician's view, or interfere with access to the surgical site.

In recent years, minimally invasive surgical approaches have been applied to orthopedic surgery and more recently to spine surgery, such as instrumented fusions involving one or more vertebral bodies. Unlike minimally invasive procedures such as arthroscopic knee surgery or gallbladder surgery where the affected area is contained within a small region of the body, spinal fusion surgery typically encompasses a considerably larger region of the patient's body. In addition, arthroscopic surgery and laparoscopic surgery permit the introduction of fluid (i.e. liquid or gas) for distending tissue and creating working space for the surgeon. Surgery on the spine does not involve a capsule or space that can be so distended, instead involving multiple layers of soft tissue, bone, ligaments, and nerves. For these reasons, the idea of performing a minimally invasive procedure on the spine has only recently been approached.

By way of example, in a typical spine fusion at least two vertebral bodies are rigidly connected using screws implanted into the respective vertebral bodies with a solid metal rod spanning the distance between the screws. This procedure is not generally conducive to a minimally invasive approach. The insertion of pedicle or facet screws is relatively straightforward and can be accomplished through a minimal incision. The difficulty arises upon the introduction of a length of rod into a very small incision with extremely limited access and visibility. A single level fusion may require a 30-40 mm rod to be introduced into a 1 cm incision and a multilevel fusion may require a rod several inches long to fit into a 1 cm incision. For this reason, it is important that the minimal incision be maintained in an open and accessible condition (i.e. as wide as practicable) for introduction of the rod.

Minimally invasive surgery offers significant advantages over conventional open surgery. First, the skin incision and subsequent scar are significantly smaller. By using more than one small incision rather than one large incision, the need for extensive tissue and muscle retraction may be greatly reduced. This leads to significantly reduced post-operative pain, a shorter hospital stay, and a faster overall recovery.

Most spine implant procedures are open procedures, and while many manufacturers advertise a minimally invasive method, the procedure is typically not recommended for fusions and focuses on more common and accepted minimally invasive spine procedures such as kyphoplasty, vertebroplasty, and discectomy.

Medtronic Sofamor Danek's SEXTANT® is a minimally invasive device used for screw and rod insertion. Its shortcomings lie with how complicated the system is to use and the requirement for an additional incision for rod introduction. This system also requires that the guidance devices be rigidly fixed to the pedicle screw head in order to maintain instrument alignment and to prevent cross-threading of the set-screw. For these reasons, the surgeon cannot access the surrounding anatomy for complete preparation of the field. Nor does SEXTANT® allow for any variation in the procedure, if need be.

Depuy Spine's VIPER™ system is another minimally invasive implant and technique recommended for one or two level spine fusions. This system is less complicated than the SEXTANT® only requiring two incisions for a unilateral, one-level fusion, but it is limited in the same way as the SEXTANT® because it also requires the instrumentation to be rigidly fixed to the pedicle screw.

Spinal Concept's PATHFINDER® and NuVasive's SPHERX® spinal system (as disclosed in U.S. Pat. No. 6,802,844), are marketed as "minimally disruptive" spine fusion implants and procedures. While they have advantages over a general "open" procedure, they do not provide all of the advantages of a truly minimally invasive approach. Their characterization as "minimally open" procedures is a result of the inherent difficulty of introducing a rod in a minimally invasive spinal procedure. In order to introduce a rod long enough to accomplish a single level fusion, these systems describe an incision long enough to accept such a rod, thereby undermining the advantages of a minimally invasive approach.

The problem of rod introduction warrants further discussion as it is the central problem in minimally invasive spinal fusions. The systems currently on the market address this issue by adding another incision, using a larger incision, or avoiding fusions greater than one level.

In order to be truly minimally invasive, a spine fusion procedure should have a minimum number of small incisions and not require significant tissue and/or muscle retraction. Furthermore, an improved approach should encompass as many variations and applications as possible thereby allowing the surgeon to adjust the procedure to accommodate the anatomy and surgical needs of the patient as presented. For instance, spinal fusions should not be limited to just one or two levels.

Therefore, a continuing need exists for an improved device, an improved system, and an improved method for performing minimally invasive spine surgery.

SUMMARY

The present disclosure is directed towards a device, a system, and a method for a screw-based retractor used in performing minimally invasive spine surgery. In some embodiments, the retractor is co-molded as part of and has blades that are frangible from, a pedicle bone screw that acts as a point of fixation with respect to the patient. The retractor acts as a guide that will aid in the insertion of instruments and implants into the anatomy of a patient.

The minimally invasive retractor has a proximal end that flexes away from the radial center. In its nominal position, the retractor will have a generally cylindrical cross-sectional configuration with at least one retracting arm extending from a pedicle tulip. In one embodiment, the retractor has a "living hinge" joining the retractor arm to a blade. The living hinge is located above the screw head and has at least one gap used to create the retractor blades. More than one living hinge can be incorporated to help facilitate bending along any portion of the blade's length. An optional window may be located between the screw head and the living hinge to allow for the insertion of instruments into the surgical site.

Instrument holes are located through the blades, perpendicular to the longitudinal axis, whereby a standard surgical instrument, such as a Gelpi Retractor, can be used to spread the blades apart for retracting the skin and soft tissue. This is done in order to maintain the field of view and/or working site.

As viewed along a longitudinal axis, the cross-section of the retractor has a generally circular configuration and provides additional stiffness. The geometry of the retractor provides sufficient stiffness for maintaining the opening at the surgical site.

The distal tip of the minimally invasive retractor is bullet shaped to aid in the retractor's insertion through the soft tissue. The distal end of each of the arms is molded onto the pedicle tulip. Alternatively, the arms of the retractor may be attached to the pedicle tulip by the use of an adhesive.

Upon completion of the procedure, the arms are separated from the pedicle tulip and pulled straight out of the incision. Co-molding the retractor as part of the pedicle screw eliminates the need for assembly during surgery and eases the removal of the blades following a surgical procedure.

Multiple retractors may be used during a single spine procedure. The retractor is manufactured for a single use.

BRIEF DESCRIPTION OF THE DRAWINGS

Embodiments of the presently disclosed minimally invasive retractor are described herein with reference to the accompanying drawings, wherein.

Other features of the present disclosure will become apparent from the following detailed description, taken in conjunction with the accompanying drawings, which illustrate, by way of example, various principles of the present disclosure.

DETAILED DESCRIPTION OF THE EMBODIMENTS

A device, system, and method for orthopedic spine surgery using a screw based retractor is described in U.S. patent application Ser. No. 11/528,223, filed Sep. 26, 2006, and published on May 10, 2007 as U.S. Published patent application No. 2007/0106123, the entire contents of which is incorporated by reference herein. The retractor is designed to be coupled with a pedicle screw and has blades that are frangible from the pedicle screw tulip. A portion of the retractor is removed from the surgical site after use.

Embodiments of the presently disclosed minimally invasive retractor will now be described in detail with reference to the drawings wherein like reference numerals identify similar or identical elements. In the drawings and in the description that follows, the term "proximal," will refer to the end of a device or system that is closest to the operator, while the term "distal" will refer to the end of the device or system that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front.

Referring initially to FIGS. 1-5, a first embodiment of the presently disclosed minimally invasive retractor or retractor is illustrated and generally designated as 100. Retractor 100 includes an open proximal end 2 and a distal end 4. A longitudinal axis is defined as extending through the center of the proximal end 2 and the distal end 4. The distal end 4 of retractor 100 is a pedicle screw tulip 10 having a generally convex outer surface that facilitates insertion of the retractor 100 through layers of body tissue. A retractor assembly includes a pedicle screw 20 that may be a monoaxial screw, as shown, or a polyaxial screw in combination with retractor 100.

A pair of arms 13 extend distally from the pedicle tulip 10. Each of the pair of arms 13 may include an optional window 12. Optional window 12 is sized and configured to receive instruments therethrough and/or permit inspection.

Figure 1:
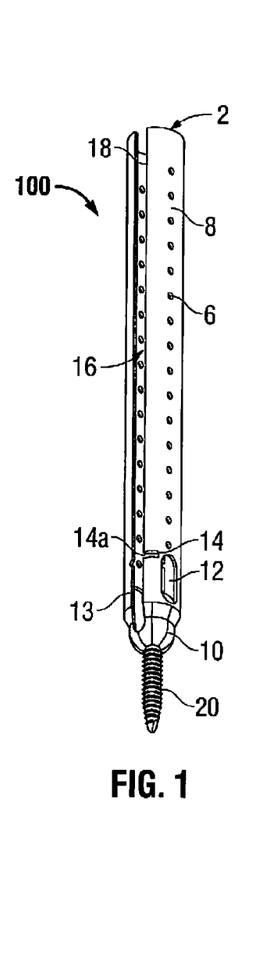
FIG. 1 is a perspective view of a minimally invasive retractor according to a first embodiment of the present disclosure.
Figure 2:
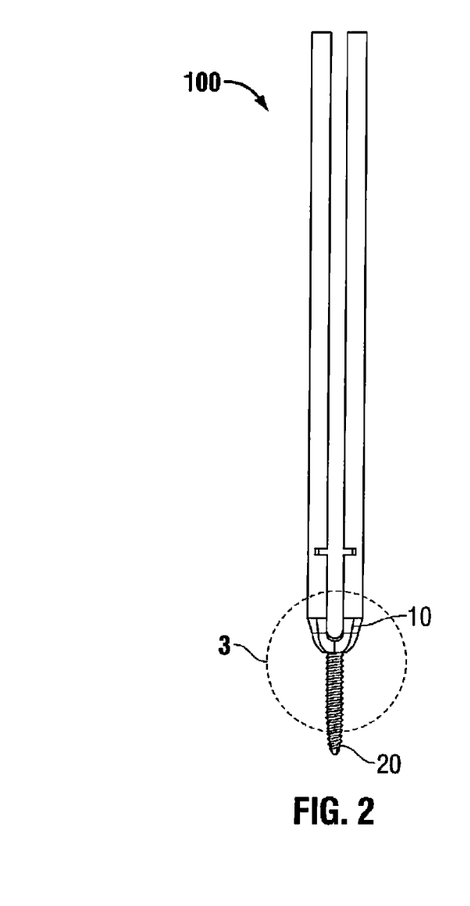
FIG. 2 is a side view of the minimally invasive retractor of FIG. 1.
Figure 3:
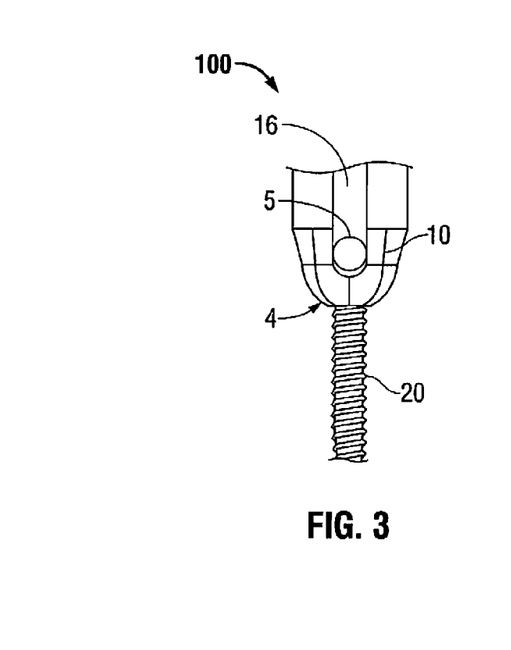
FIG. 3 is an enlarged side view of the detailed area "3" of FIG. 2.

Each of the arms 13 may extend to an optional flexible region or living hinge 14, defined by a pair of recesses 14a on each side of the living hinge 14. As illustrated in FIG. 2, a retractor blade 8 is attached to and extends from the living hinge 14 to define a substantially continuous elongate member. In addition, retractor 100 includes a pair of retractor blades 8 having a plurality of instrument holes 6 disposed on each of retractor blades 8. Instrument holes 6 are configured and dimensioned to cooperate with different surgical instruments.

The retractor 100 has a substantially circular cross-section. Each blade 8 and arm 13 set has an arcuate cross-sectional configuration that is less than about 180°. A pair of continuous slots 16 separate one blade 8 and arm 13 set from the other blade 8 and arm 13 set.

The pair of continuous slots 16 define a passage 18 that extends substantially the entire length of retractor 100. Passage 18 is expandable for receiving a rod 5 therein. Retractor blades 8 and arms 13 define a substantially circular ring shape, thereby providing sufficient stiffness (i.e. rigidity) such that retractor blades 8 and arms 13 resist bending from the counter forces of the retracted tissues.

Retractor 100 is formed on or over the pedicle tulip 10 from a suitable biocompatible material that is sterilizable in a suitable configuration and thickness so as to be sufficiently rigid to provide retraction of tissue, and yet is sufficiently bendable to be spread apart to provide retraction and to be forcibly separated from the pedicle tulip 10 as necessary and appropriate. It is contemplated that retractor 100 be formed from polymers such as polypropylene, polyethylene, or polycarbonate; silicone; polyetheretherketone ("PEEK"); titanium; titanium alloy; surgical steel; or other suitable material including a combination of materials. The arms 13, blades 8, and tulip 10 may be formed from the same or different material.

Each retractor blade 8 is capable of being bent away from the centerline of retractor 100 assisted by an optional living hinge 14, in response to applied forces. Bending retractor blade 8 away from the centerline (i.e. radially outwards) increases the width of the passage 18 and acts to retract the surrounding tissue at the selected surgical site.

Figure 4:
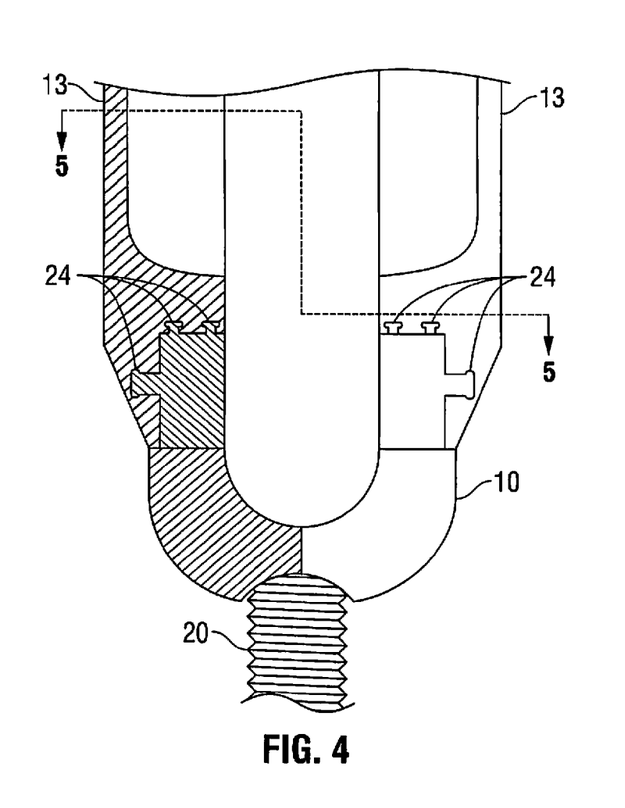
FIG. 4 is an enlarged side cross-sectional view of the minimally invasive retractor of FIG. 3.
Figure 5:
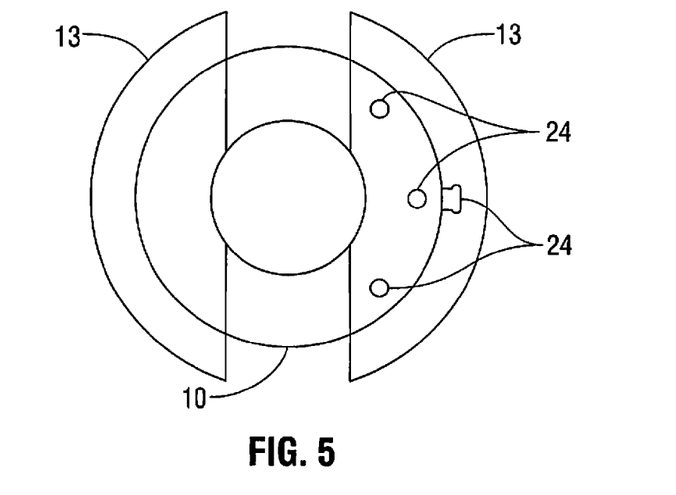
FIG. 5 is a top cross-sectional view of a minimally invasive retractor of FIG. 4 taken along section line 5-5.

The tulip 10 may be formed with protrusions 24 extending from the top and sides. These protrusions are formed such that the end furthest from the tulip 10 has a larger diameter than the end closest to the tulip 10, resulting in a bulb shaped structure. The force of retraction is leveraged off of the pedicle screw 20 itself and the bulb shaped protrusions 24 increases the amount of force needed to separate the arm 13 from the tulip 10. Preferably, the tulip 10 is placed in a mold and the arms 13 and blades 8 are molded onto the tulip 10. The tulip 10 may be combined with the pedicle screw either before or after the arms are formed.

Removal of the arms 13 and blades 8 from the surgical site is accomplished by pulling the arms 13 proximally (i.e. away from the pedicle screw 20) from the pedicle tulip 10. A separating tool may be used to pry the arms 13 from the pedicle tulip 10. The separate leveraging tool is placed between the arms 13 and tulip 10 to exert counterforces to cause the arms to separate from the tulip 10 at the attachment points. After separating the arms 13, the physician can readily remove the separated arms 13 from the surgical site while leaving the pedicle tulip 10 and pedicle screw 20 at the surgical site.

Figure 6:
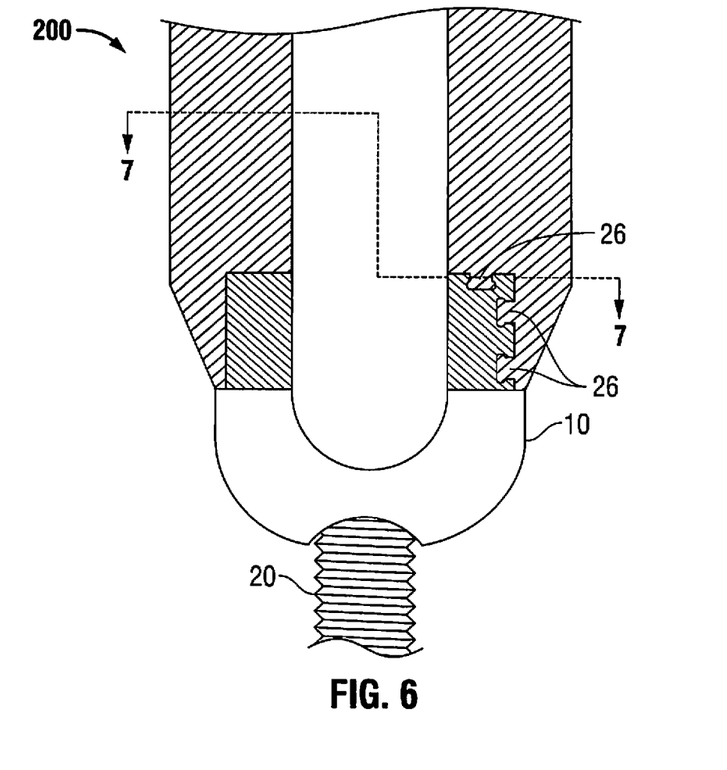
FIG. 6 is an enlarged side cross-sectional view of a distal region of a second embodiment of the minimally invasive retractor of the present disclosure.
Figure 7:
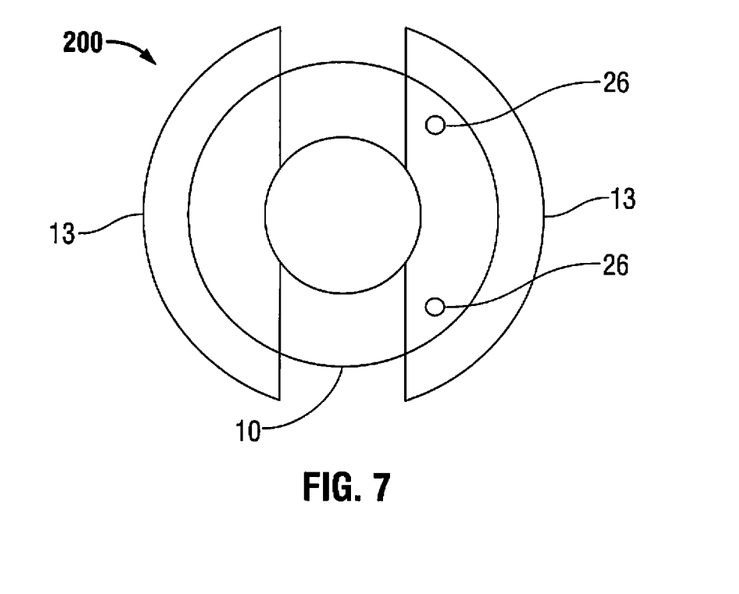
FIG. 7 is a top view of the minimally invasive retractor of FIG. 6.

Referring now to FIGS. 6-7, a second embodiment of the present disclosure is illustrated as retractor 200 having an open proximal end 2. Similar to retractor 100, the distal end has a pair of arms 13 that extend from the tulip 10.

As in the previous embodiment, blades 8 have an arcuate configuration that is less than about 180° and are radially spaced apart to define a pair of continuous slots 16 along a substantial portion of retractor 200. Additionally, retractor blades 8 define a passage 18 through retractor 200.

In this embodiment, the tulip 10 is formed with a plurality of recesses 26 in the top and sides to allow the material to flow into the recesses during formation of the arms 13 and blades 8 in order to secure the arms 13 to the tulip 10. Alternatively, the recesses 26 may be machined into the tulip 10. The blades 8 can also be formed on the tulip 10 either prior to assembly with the pedicle screw 20 or after assembly.

Removal of the blades 8 from the pedicle tulip 10 and the surgical site is accomplished by either pulling the blades 8 proximally or by using a tool to pry the blades 8 from the pedicle tulip 10.

Figure 8:
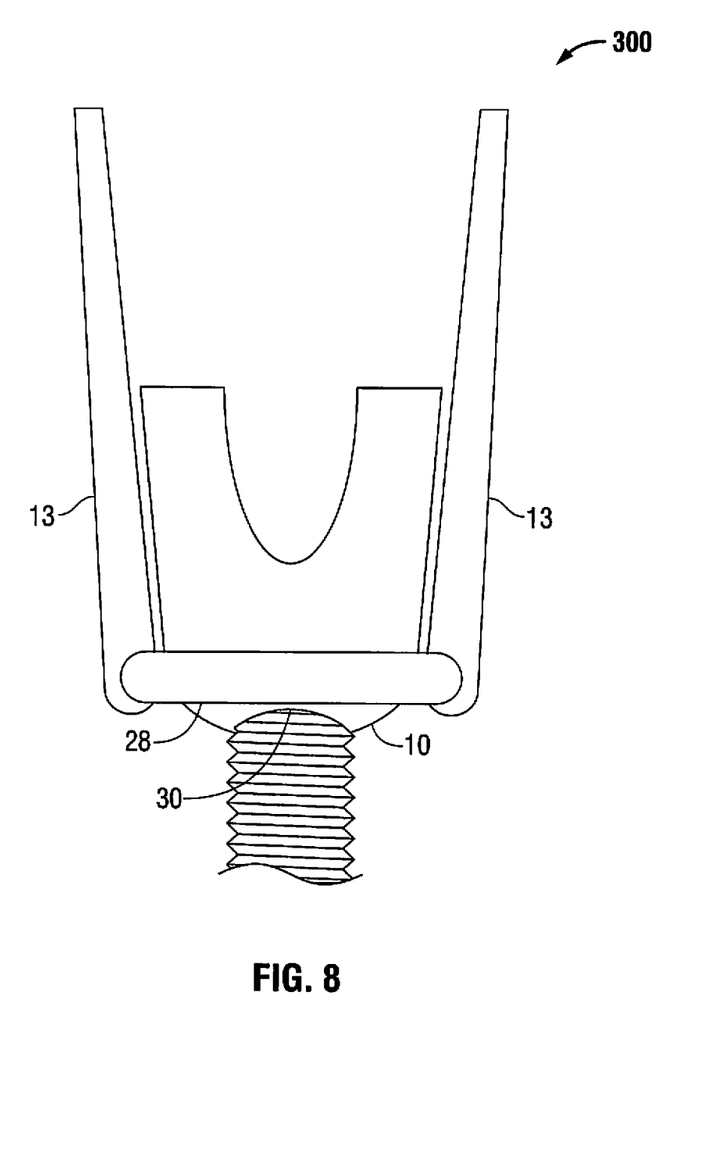
FIG. 8 is a side view of a third embodiment of the minimally invasive retractor of the present disclosure.

In still another embodiment, referring now to FIG. 8, the blades 8 of retractor 300 are molded onto a washer 28. The washer 28 has an opening diameter larger than the pedicle screw opening 30 located in the most distal end of the pedicle tulip 10, but smaller than the major diameter of the pedicle tulip 10. Upon completion of the surgery the blades 8 are pulled up and over the tulip 10 until the arms break away from the washer 28 and are able to be removed from the surgical site. The washer 28 remains seated around the base of the pedicle screw 20.

The retractor may, alternatively, include two blades integrally formed and attached on only one side of the tulip, thereby increasing the lateral opening near the tulip and defining a window that is larger than previously disclosed window 12. This embodiment provides increased access to the target site, thereby allowing larger implants or instruments to be positioned in the target site.

Alternatively, the presently disclosed retractor includes only one retractor blade and is attached to the pedicle tulip by an adhesive. The adhesive changes state in the presence of either a solvent or an ultraviolet light. This configuration allows greater variability in creating the retracted space as well as increasing access to the target site for using larger instruments or inserting larger devices than possible with retractor 100.

The blades may extend circumferentially over the sides of the pedicle tulip to below the equator of the tulip to a region where the tulip narrows (i.e. towards the distal narrowed tip of the bullet of the tulip) where the blades are circumferentially connected to each other around the tulip to hold the retractor with the tulip. This design allows projections or recesses, if used, to be located low around the sides of the pedicle screw tulip. This configuration also provides the retractor with a pivot point distally further than the top of the pedicle screw tulip.

It is contemplated that microchips be molded into the arms of the retractor. These microchips may collect data, such as the temperature of the body, and relay the information to a display for the surgeon. Microchips can also be used to measure the relationship of one retractor in regard to another retractor also having a microchip.

It is further contemplated that any of the previously disclosed retractors may be formed of a bendable resilient material such that when external spreading forces (e.g. from a Gelpi retractor or the physician's hands) are removed, the retractor blades will return towards their initial position (e.g., substantially parallel to the centerline). It is also contemplated that any of the previously disclosed retractors may be formed of a bendable non-resilient material such that when the external spreading forces are removed, the retractor blades resist returning to their initial position and remain in the retracted position.

The presently disclosed retractors utilize, but are not limited to, a method whereby an initial incision is made in the skin of approximately 10-15 mm in length. Surgeon preference will dictate the need for one or more stages of dilators to aid in expanding the wound before introducing one or more retractors. Normal surgical techniques may be used to close the incision(s).

Figure 9:
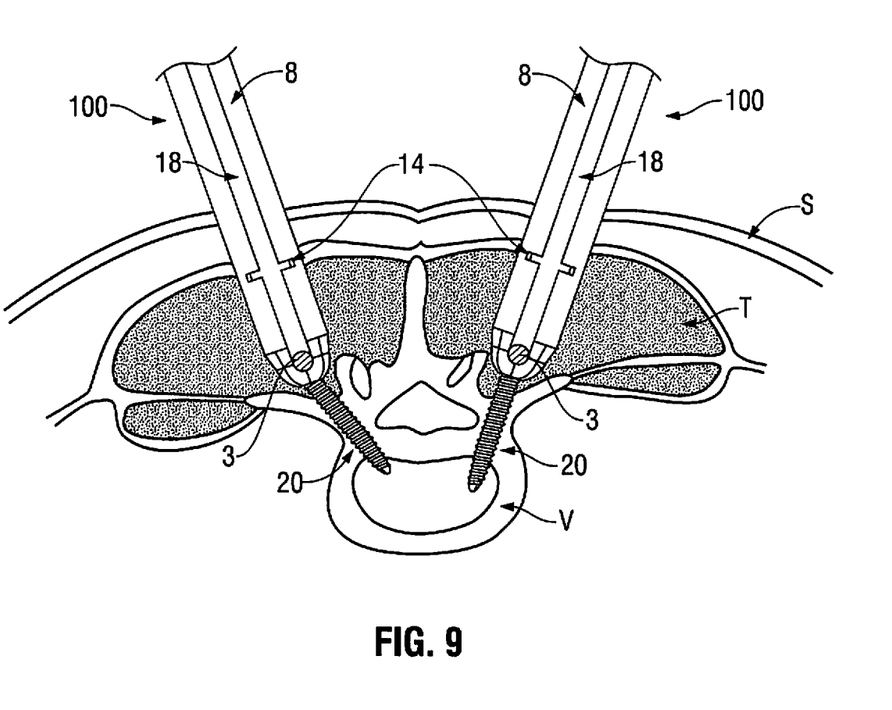
FIG. 9 is a cross-sectional side view of the minimally invasive retractor of FIG. 1 in use.

A method for use of the presently disclosed system will now be described with reference to FIG. 9. The assembled apparatus is inserted into an incision through the patient's skin S and muscle/fat tissue T such that pedicle screw 20 is subsequently threaded into a vertebral body V. Once the desired number of retractors 100 are affixed to vertebral bodies V, retractor blades 8 are spread and/or pivoted apart to retract skin S and tissue T to create a retracted area at the target site. Rod 3 is inserted in pasage 18 when passage 18 is in an expanded state (i.e., tissue has been retracted).

The rod may be inserted along a path from one screw head to another, possibly subcutaneously such that it may be secured to fastening regions of pedicle screws in adjacent vertebral bodies. The retractors of the present disclosure are well suited for such a technique due to the unique access provided. Once the screw-rod construct is complete, the retractor blades 8 and/or arms 13 are separated, as described above, from the tulip 10, and then pulled out of the incision.

Removal may be done by hand or with suitable gripping tools. An example of a retractor extracting tool is described in U.S. Published patent application No. 2007/0106123 (referenced hereinabove). The blades 8 and/or arms 13 are separated from pedicle tulip 10 without imparting significant downward or rotational forces against the patient's body. Retractor 100 may then be removed from the patient and this process may be repeated for each installed retractor 100.

The retractor blades may be transparent or opaque and may have radio opaque markers for visibility during various imaging techniques. In addition, the blades may have a reflective or non-reflective coating to increase visibility in the surgical site and may have an artificial lighting feature.

As with any surgical instrument and implant, the retractors must have the ability to be sterilized using known materials and techniques. Parts may be sterile packed by the manufacturer or sterilized on site by the user. Sterile packed parts may be individually packed or packed in any desirable quantity. For example, a sterile package may contain one or more retractors in a sterile enclosure. Alternatively, such a sterile surgical kit may also include one or more bone biopsy needle(s), Jamshidi needle(s), guide wires, detachment tools, sterile cannulated scalpels, dilators, rods, or other surgical instruments and combinations thereof.

The blades may be made of a light transmitting material. The retractor may include a light guide system. The light guide system has an input adapter to receive light from a light source and one or more light emitting surfaces to illuminate the surgical field.

Further still, it will be appreciated that the pedicle screw may be cannulated such that it may be translated along a guide wire, thereby facilitating percutaneous insertion of the pedicle screw and retractor. In addition, it is contemplated that conventional insertion tools or those disclosed in U.S. patent application Ser. No. 12/104,653, filed on Apr. 17, 2008, and published on Oct. 23, 2008 as U.S. Published patent application No. 2008/0262318, the entire contents of which are hereby incorporated by reference, may be used in conjunction with the presently disclosed retractor and pedicle screws.

It will be understood that various modifications may be made to the embodiments of the presently disclosed retraction system. Therefore, the above description should not be construed as limiting, but merely as exemplifications of embodiments. Those skilled in the art will envision other modifications within the scope and spirit of the present disclosure.

For example, while the foregoing description has focused on spine surgery, it is contemplated that the retractors and methods described herein may find use in other orthopedic surgery applications, such as trauma surgery. Thus, where it is desired to insert a screw or pin into bone in a minimally invasive manner, or otherwise to access a surgical target site over a guidewire, the dilator, scalpel and retractors (or some of them) of the present disclosure may be used, with or without a bone screw.

What is claimed is:

1. A method of fabricating a screw based retractor comprising:
    a) providing a pedicle screw tulip having a side surface extending between a distal end configured to couple to a pedicle screw and a proximal end surface configured with at least one attachment feature selected from a series of protrusions extending proximally from the proximal end surface and a series of indentations extending distally from the proximal end surface;
    b) placing the tulip within an injection mold; and
    c) injecting a material through the injection mold, wherein the material interacts with the at least one attachment feature and forms at least one arm extending from the tulip such that the at least one arm is removably affixed to the tulip at a frangible joint.

2. The method of claim 1, further comprising assembling the pedicle screw within the tulip.

3. The method of claim 1, further comprising forming the at least one arm to include a flexible joint region.

4. The method of claim 1, wherein the series of protrusions are generally bulb-shaped.

5. The method of claim 1, wherein the series of protrusions have a larger diameter at an end furthest from the tulip than at an end closest to the tulip.

6. The method of claim 1, wherein the series of indentations are machined into the tulip.

7. The method of claim 1, wherein the tulip is formed from a material that is different than a material from which the at least one arm is formed.

8. The method of claim 1, wherein the at least one arm is formed to extend proximally from the tulip.

9. The method of claim 1, further comprising molding at least one microchip into the at least one arm, the microchip configured to collect data.

10. The method of claim 1, further comprising forming the at least one arm of a bendable resilient material.

11. The method of claim 1, further comprising forming the at least one arm of a bendable non-resilient material.

12. The method according to claim 1, wherein the frangible joint is a living hinge.

13. The method according to claim 1, wherein the distal end of the tulip is convex.

14. The method according to claim 1, wherein the tulip is further configured with the at least one attachment feature disposed on the side surface thereof.

15. The method according to claim 1, wherein the proximal end surface is a flat surface.

16. The method according to claim 1, wherein the side surface is configured with at least one attachment feature selected from a series of protrusions extending from the side surface and a series of indentations extending from the side surface.

17. A method of fabricating a screw based retractor comprising:
    a) providing a pedicle screw tulip having a distal end configured to couple to a pedicle screw and extending proximally to terminate in a proximal end surface, the distal end having a washer disposed thereon;
    b) placing the pedicle tulip within an injection mold; and
    c) injecting a material through the injection mold, wherein the material interacts with the washer and forms at least one arm extending from the washer such that the at least one arm is removably affixed to the pedicle tulip at a frangible joint.

18. The method of claim 17, further comprising assembling the pedicle screw within the tulip.

19. The method of claim 17, further comprising forming the at least one arm to include a flexible joint region.

20. The method according to claim 17, wherein the frangible joint is a living hinge.

* * * * *